United States Patent
Zhang et al.

(10) Patent No.: US 10,571,370 B2
(45) Date of Patent: Feb. 25, 2020

(54) METHODS AND MACHINES FOR DRYING BLOOD SMEARS AND AN AUTOMATIC SMEARING DEVICE

(71) Applicant: SHENZHEN MINDRAY BIO-MEDICAL ELECTRONICS CO., LTD., Shenzhen (CN)

(72) Inventors: Liang Zhang, Shenzhen (CN); Xuerong Li, Shenzhen (CN); Yuan Xiang, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 0 days.

(21) Appl. No.: 15/271,097

(22) Filed: Sep. 20, 2016

(65) Prior Publication Data

US 2017/0010192 A1    Jan. 12, 2017

Related U.S. Application Data

(63) Continuation of application No. PCT/CN2014/073774, filed on Mar. 20, 2014.

(51) Int. Cl.
| | |
|---|---|
| G01N 1/30 | (2006.01) |
| F26B 3/04 | (2006.01) |
| G01N 1/28 | (2006.01) |
| F26B 9/06 | (2006.01) |

(52) U.S. Cl.
CPC ............ *G01N 1/2813* (2013.01); *F26B 3/04* (2013.01); *F26B 9/06* (2013.01)

(58) Field of Classification Search
None
See application file for complete search history.

(56) References Cited

U.S. PATENT DOCUMENTS

| | | | | |
|---|---|---|---|---|
| 4,096,824 A | * | 6/1978 | Levine | G01N 1/2813 118/100 |
| 5,356,595 A | | 10/1994 | Kanamori | |
| 5,766,549 A | * | 6/1998 | Gao | G01N 1/2813 118/100 |
| 7,297,311 B2 | * | 11/2007 | Tamura | G01N 1/2813 422/519 |
| 2009/0155841 A1 | * | 6/2009 | Yamasaki | G01N 1/2813 435/40.51 |

FOREIGN PATENT DOCUMENTS

| | | | |
|---|---|---|---|
| CN | 202024918 U | 11/2011 | |
| CN | 202869177 U | 4/2013 | |
| JP | 03-033655 | 2/1991 | |
| WO | WO-9957538 A1 * | 11/1999 | ........... G01N 1/2813 |

OTHER PUBLICATIONS

CN 202869177; English translation accessed May 26, 2018 at: https://patents.google.com/patent/CN202869177U/en?oq=CN202869177).*
Hoppe et al., Iowa State University Veterinarian, vol. 40, No. 3, Article 10, pp. 113-116 (1978).*
Hoppe et al., Iowa State University Veterinarian, vol. 40, No. 3, Article 10, pp. 113-116 (1978) (of record).*
CN 202869177; English translation accessed May 26, 2018 at: https://patents.google.com/patent/CN202869177U/en?oq=CN202869177) (of record).*

* cited by examiner

*Primary Examiner* — Soren Harward
*Assistant Examiner* — Paul D. Pyla
(74) *Attorney, Agent, or Firm* — Kory D. Christensen

(57) ABSTRACT

A method and a machine for drying blood smears and an automatic smearing device are provided. In the method, a dry gas is used as a drying medium to dry a blood film on a blood smear in drying the blood smear, thus reducing drying time and the number of blood smears which are dried together. The dry gas is obtained by: first, removing a liquid from a pressurized gas, second, filtering a vapor, and finally, decompressing the dried pressurized gas to be a non-pressurized gas having lower humidity. In addition, the dry gas is further heated for further reducing the humidity of the dry gas. In order to prevent cell distortion from occurring, the heated dry gas is caused to gently flow over the blood smear in a direction which the blood film is spread.

12 Claims, 3 Drawing Sheets

METHODS AND MACHINES FOR DRYING BLOOD SMEARS AND AN AUTOMATIC SMEARING DEVICE

TECHNICAL FIELD

The present disclosure relates to the field of medical technology, more particularly to techniques for drying blood smears.

BRIEF SUMMARY

The present disclosure relates to methods and machines for blood analysis. More particularly, the present disclosure relates to method for drying blood smears and machines using the methods for drying blood smears. The present disclosure also relates to an automatic smearing device for making a blood smear.

In one aspect of the present disclosure, a method for drying blood smears includes providing a blood smear having a blood film on a major surface of a slide; acquiring a dry gas for drying the blood smear; and having the dry gas flow over the major surface of the slide.

In another aspect of the present disclosure, a machine for drying blood smears may include a gas inlet and a drying body. The gas inlet is used to acquire a dry gas, and the drying body is used to insert a blood smear for drying. The drying body may include an inlet for flowing the dry gas into the drying body and an outlet for flowing the dry gas out of the drying body. The dry gas is transferred into the drying body through the gas inlet and the inlet of the drying body. The inlet and outlet of the drying body are arranged to have the dry gas form a gas flow in a direction along which a blood film to be dried is spread.

In still another aspect of the present disclosure, an automatic smearing device may include a blood smear maker module which makes a blood smear; a staining module which stains the blood smear; and at least one of the above machines for drying blood smears, which dries the blood smear.

DETAILED DESCRIPTION

In some clinical examination, a drop of blood on a slide is spread to be a film usually called a blood film, and the slide with a blood film is called a blood smear. It is known that the blood smear needs to be dried sufficiently before being stained; otherwise the blood film of the blood smear might separate from the slide which supports the blood film.

Some automatic smearing devices dry blood smears by air drying at present. But the air drying method has an unsatisfying drying speed. So a plurality of blood smears are dried simultaneously so that each blood smear can have enough time to dry. When many blood smears are dried simultaneously, blood smears located in an outer boundary might be dried too much to obtain a good blood smear. And when a drying machine fails, those blood smears dried simultaneously might all be destroyed. There is another air drying method to dry blood smears more quickly, wherein air is sucked away by an electric fan.

Therefore, the present disclosure provides methods and machines for drying blood smears, and an automatic smearing device, which reduces drying time the number of blood smears dried simultaneously, reduce cell distortion, and obtain good blood smears.

The following embodiments illustrate various features of the present invention.

In the present disclosure, a dry gas is used to dry a blood film of a blood smear and transferred into a drying body for drying a blood smear, where the dry gas could carry moisture away from the blood film of the blood smear. It is already proved by tests that a drying time period using a dry gas could be one tenth of that using a traditional air drying method, and could be one third of that of drying by an electric fan.

Cell distortion may occur when the blood smear is dried by an electric fan. Cells in the blood film are rather soft before the blood film is dried, and cell distortion occurs because the electric fan causes the air to be turbulent. Surprisingly, it was discovered that the cells could keep their original morphology if the air flowed in a direction along which the blood film was spread. Moreover, it was discover that a dry gas is a better drying medium for drying the blood smear. A blood smear was obtained more quickly and found to be of better quality when a blood smear was inserted into a drying body and the dry gas formed a gas flow which gently blows the blood film of the blood smear in a direction along which the blood film was spread.

EXAMPLE 1

Figure 1:
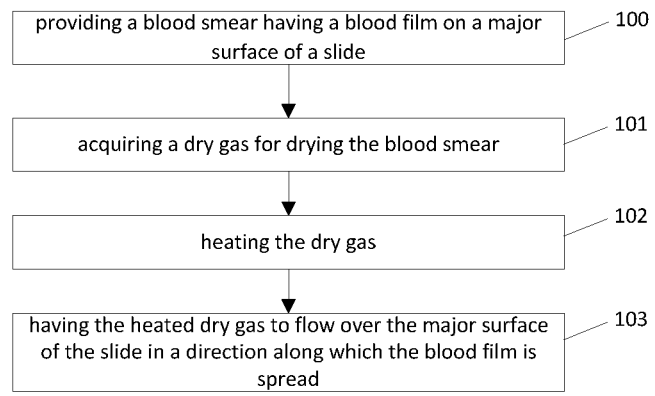
FIG. 1 is a flow diagram which shows a method for drying blood smears in accordance with Example 1 of the present disclosure.

Example 1 illustrates a method for drying blood smears, as shown in FIG. 1. The method may include the following steps:

100, providing a blood smear having a blood film on a major surface of a slide;

101, acquiring a dry gas for drying the blood smear;

102, heating the dry gas; and 103, having the heated dry gas flow over the major surface of the slide in a direction along which the blood film is spread.

In step 100, a drop of blood is dropped onto a major surface of a slide, and smeared by a spreader. The blood is spread to be a blood film on the major surface.

In step 101, a dry gas is used to dry the blood smear. In Example 1, a dry gas of atmospheric pressure is used as a drying medium to dry the blood smear, for example, a gas of atmospheric pressure is filtered and dried to be the dry gas.

Figure 2:
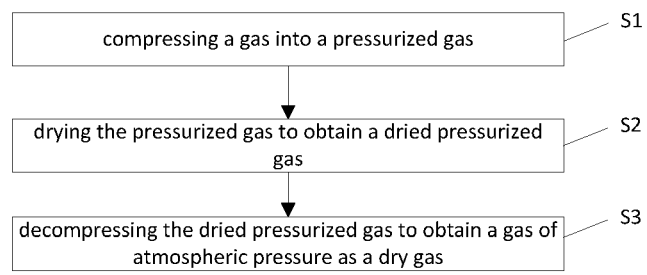
FIG. 2 is a flow diagram which shows a method for acquiring a dry gas in accordance with an embodiment of the present disclosure.

Alternatively, a dry gas could be prepared as a method shown in FIG. 2.

S1, compressing a gas into a pressurized gas.

S2, drying the pressurized gas to obtain a dried pressurized gas. For example, the pressurized gas is filtered by an aero-filter to remove most of the liquid and dirt, and then filtered by a dryer to remove most of the vapor, so as to obtain the dried pressurized gas having a very low dew point.

S3, decompressing the dried pressurized gas to obtain a gas of atmospheric pressure as a dry gas. Humidity of the dry gas will further reduce, when the dried pressurized gas is decompressed to be the gas of atmospheric pressure by a pressure regulator valve. For example, if a dried pressurized gas whose pressure is three times atmospheric pressure is decompressed to be a gas of atmospheric pressure, the humidity of the gas of atmospheric pressure is one third of that of the dried pressurized gas.

In step 102, the dry gas is heated. For example, the dry gas is heated by a heater to obtain a heated dry gas.

In step 103, the heated dry gas is driven to flow over the major surface of the slide in a direction along which the blood film is spread. The heated dry gas is transferred into a drying body for drying the blood smear. When the blood smear is inserted into the drying body, the heated dry gas can form a gas flow between the blood smear and a wall of the drying body. There is an inlet for flowing the heated dry gas into the drying body and an outlet for flowing the heated dry gas out of the drying body. The inlet and outlet of the drying body are arranged to have the heated dry gas gently flow over a major surface of the blood smear to dry it in a direction along which the blood film is spread.

In the present disclosure, a dry gas having very low humidity could be obtained by three steps: first, removing a liquid from a pressurized gas; second, removing a vapor from the pressurized gas; and third, decompressing the gas to be the dry gas. The dry gas is a better drying medium which could greatly reduce a drying time period.

In the present disclosure, the dry gas flows over the blood film in a direction along which the blood film is spread. In other words, a flow direction of the dry gas identifies with the direction which the blood film is spread. It is proved by tests that the blood smear can be dried sufficiently and cells in the blood film will not be deformed. Thus, the blood smear could be dried well by this method, and the blood smear will be stained more easily to obtain a clear blood smear without cell distortion for microscope examination.

In the example, the dry gas is heated to accelerate the drying process before it flows over the blood film.

In another example, in order to further prevent the gas flow from destroying morphology of cells in the blood film, a flow rate and discharge of the dry gas could be adjusted to form a gentle flow before it is heated.

In the foregoing example, only one blood smear to be dried is inserted into the drying body in a single drying processing session to maximally avoid turbulent flow.

EXAMPLE 2

Figure 3:
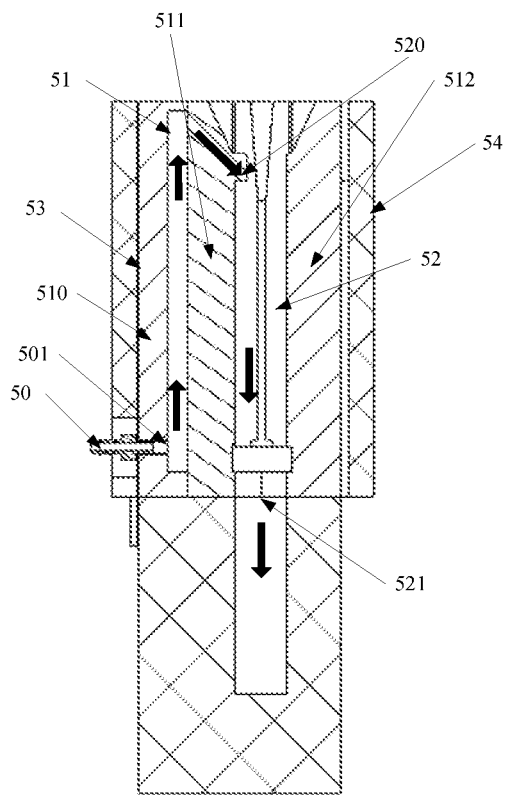
FIG. 3 is a cut-away view which shows a machine for drying blood smears in accordance with Example 2 of the present disclosure.

A machine for drying blood smears is provided in Example 2, as shown in FIG. 3, which can execute the above method for drying blood smears. FIG. 3 is a cut-away view which shows the machine. The machine may include a gas inlet 50, a preheat channel 51, a drying body 52 and a heater 53.

The gas inlet 50 can transfer a dry gas. The preheat channel 51 can connect with the gas inlet 50, by which the dry gas is transferred and heated.

The heater 53 is attached to a wall of the preheat channel 51, or is disposed inside the preheat channel 51. The heater 53 can heat the dry gas passing through the preheat channel 51. The heater 53 could be a heating plate, a heating film or a heating wire.

The drying body 52 can have walls and a space inside, where the blood smear is inserted to be dried. The drying body 52 may include an inlet 520 for flowing the heated dry gas into the drying body 52 and an outlet 521 for flowing the heated dry gas out of the drying body 52. The inlet 520 of the drying body 52 can connect with an outlet 501 of the preheat channel 51, so that the heated dry gas can be transferred into the drying body 52. Respective locations of the inlet 520 of the drying body 52 and the outlet 521 of the drying body 52 are arranged to have a dry gas form a gas flow in a direction along which a blood film to be dried is spread. In the example, the space in the drying body 52 is enough for holding only one blood smear and a single slit open for inserting the blood smear into the space. So only one smear is inserted into the drying body 52 in a single drying processing to maximally avoid turbulent flow. It will be appreciated by those skilled in the art that more than one blood smear could be dried at the same time if the gas flow could be controlled well and the extent of the cell distortion is acceptable.

In Example 2, the preheat channel 51 and the drying body 52 are built by a first cavity wall 510, a second cavity wall 511 and a third cavity wall 512. The gas inlet 50 can connect with the preheat channel 51 at one end of the preheat channel 51, and the drying body 52 can connect with the preheat channel 51 at another end of the preheat channel 51, so that the dry gas can be sufficiently heated in the preheat channel 51. In an alternative example, a preheat channel can be a cavity which surrounds walls of the outside drying body in a spiral manner.

In Example 2 as shown in FIG. 3, arrows indicate a flow direction of the dry gas. In general, there is a reserved area for marking the sample number on one end of a slide's long side, and a drop of blood usually is spread from this area to another end of the slide's long side. A transferring machine, such as a mechanical hand, will catch the slide by this reserved area, so that it is usually out of the drying body. So basically, when a blood smear is inserted into the drying body 52 from top to bottom, a direction which a blood film is spread is also from top to bottom. Therefore, in order to have the dry gas gently flow over a major surface of the blood smear from the top to bottom, the inlet 520 of the drying body 52 should be located on the top of the drying body 52, and the outlet 521 of the drying body 52 should be located on the bottom of the drying body 52. In an alternative example, when a blood smear is inserted into a drying body from bottom to top, a direction which a blood film is spread is also from bottom to top. In order to have a dry gas gently flow over a major surface of a blood smear from bottom to top, the inlet of the drying body should be located on the bottom of the drying body, and the outlet of the drying body should be located on the top of the drying body. It will be appreciated by those skilled in the art that how an inlet and an outlet of the drying body are designed could depend on a manner in which a blood smear is inserted into the drying body.

In Example 2 as shown in FIG. 3, an angle between the blood smear and an axis of an inlet of a drying body is less than 90 degrees. Cells of a blood film are rather soft before the blood film is dried. If a dry gas flows aslant a blood smear, a cell distortion of the blood film might less occur less. Accordingly, an axis between the inlet 520 of the drying body 52 and the blood smear may be less than 90 degrees for reducing the cell distortion of the blood film.

In other exemplary embodiments, a heater could include a heater control and a temperature sensor which is disposed in a preheat channel, which are not shown. An output terminal of the temperature sensor can couple to the heater control. The heater control can control a heater to power on and off by a temperature detected by the temperature sensor. The heater control can control the heater to power off when the detected temperature of the preheat channel 51 reaches a first predetermined value. The heater control can control the heater to power on when the detected temperature of the preheat channel 51 reaches a second predetermined value. So a temperature of the preheat channel 51 and the drying body 52 will remain constant.

In another exemplary embodiment, a machine of the present disclosure can further include a heat preservation layer, which wraps the preheat channel 51, the heater 53 and the drying body 52 together. The heat preservation layer is made of a thermally non-conductive material, which can prevent heat emission and keep the preheat channel 51 and the drying body 52 at a constant temperature.

Figure 4:
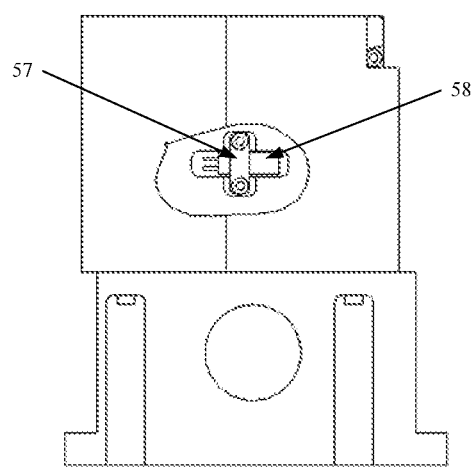
FIG. 4 is a side view which shows a machine for drying blood smears in accordance with an embodiment of the present disclosure.

Moreover, the machine of the present disclosure can further include a temperature protection switch 58 and a mount piece 57, as shown in FIG. 4. The switch 58 could be mounted on an outside shell of the machine for drying blood smears by the mount piece 57. The switch 58 is cascaded between the temperature sensor and a power source. When the temperature sensor fails, the machine will be powered off to prevent the blood smear from being over-heated. The switch 58 could be a safety fuse.

Figure 5:
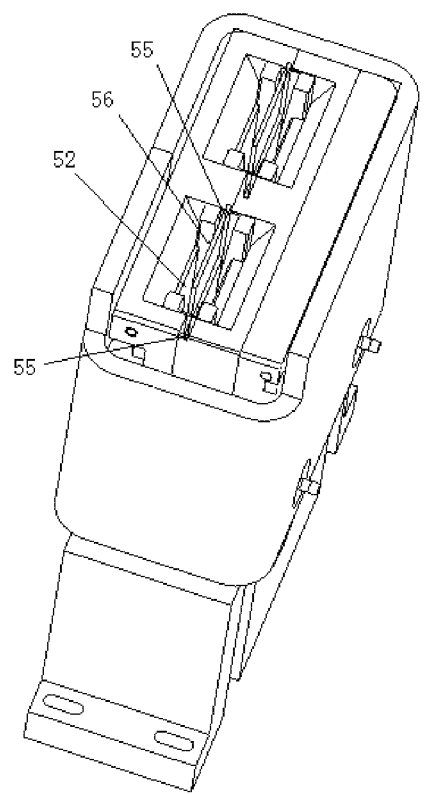
FIG. 5 is a three-dimensional view which shows a machine for drying blood smears in accordance with an embodiment of the present disclosure.

Two sides of a drying body will touch sides of a blood smear when the blood smear is inserted into the drying body. In an exemplary example, as shown in FIG. 5, there is a guide slot 55 in the two sides of a drying body 52, which touches the blood smear 56 when it is inserted into the drying body 52. The guide slot 55 is made of a wear-resistant material. The blood smear 56 merely touches the guide slot 55 when it is inserted. The abrasion-proof guide slot 55 not only prolongs the working life of the machine but also reduces processing difficulty.

In another exemplary embodiment, the gas inlet 50 could have a damper tube. A pressure sensor is disposed in the damper tube, and a flow rate or flow discharge of dry gas can be adjusted according to a pressure detected by the pressure sensor. As a result, the gas in the preheat channel would form a gentle flow for further reducing cell distortion.

In a machine for drying blood smears of the present disclosure, a dry gas is used as a drying medium, heated by a heater and kept at a constant temperature. An inlet and outlet of a drying body are arranged to have the dry medium flowing over the blood smear in a direction along which a blood film is spread. Then, the blood smear could be dried sufficiently and cells in the blood film could maintain their original morphology at the same time, so that the quality of the blood smear is improved.

In addition, a dry gas is heated to keep a flow at a constant temperature over a blood film. On the one hand, this heated dry gas could accelerate the drying processing. On the other hand, it could keep the whole drying body warm so that the blood film dries more quickly because warm walls of the drying body could bring thermal radiation to the blood film.

The above machine for drying blood smears could be used in an automatic smearing device. The automatic smearing device may include a blood smear maker module, a staining module and at least one of the machines described above. The staining module can stain a blood smear. The blood smear maker module may include several components to execute movements, such as sampling blood, dropping blood, and spreading blood to form a blood film. The machine can dry blood smears. The automatic smearing device can further include a gas distribution module which can provide a dried pressurized gas. An outlet of a gas distribution module can connect to the gas inlet in the machine for drying blood smears. There are several kinds of commercial automatic smearing devices available. A blood smear maker module and staining module of these commercial devices could be used in the present disclosure.

In an automatic smearing device of the present disclosure, a dry gas is used as a drying medium, heated by a heater and kept at a constant temperature. An inlet and outlet of a drying body are arranged to have the dry medium flow over the blood smear in a direction along which a blood film is spread. Then, the blood smear could be dried sufficiently and cells in the blood film could maintain their original morphology at the same time, so that the quality of the blood smear is improved.

The above embodiments illustrate various features of the present disclosure, which are described in detail, but are not intended in any way to limit the scope of the invention as set forth in the claims. It will be appreciated by those skilled in the art that various changes, alterations and modifications may be made to the present disclosure without departing from the spirit and scope of the present disclosure as claimed.

The invention claimed is:

1. A method for drying a blood smear, said method comprising:
    placing a blood drop on one end of a slide on a major surface of the slide;
    spreading the blood drop substantially in a direction from the one end of the slide to another end of the slide, so that a blood smear having a blood film formed by the blood drop on the major surface of the slide is obtained;
    acquiring a dry gas for drying the blood smear; and
    flowing the dry gas over the major surface of the slide from the one end of the slide to the another end of the slide in substantially the same direction that the blood drop was spread.

2. The method according to claim 1, further comprising:
    providing a drying body in which the blood smear to be dried is inserted;
    transferring the dry gas into the drying body; and
    having the dry gas flow in the direction along which the blood film is spread inside the drying body.

3. The method according to claim 2, further comprising:
    heating the dry gas before having the dry gas flow in the direction along which the blood film is spread.

4. The method according to claim 3, further comprising:
    adjusting a flow rate to a predetermined value before heating the dry gas.

5. The method according to claim 2, further comprising:
    forming a gas flow from the dry gas between the blood film of the blood smear and a wall of the drying body.

6. The method according to claim 2, wherein only one blood smear is inserted into the drying body in a single drying processing.

7. The method according to claim 1, wherein acquiring a dry gas for drying the blood smear comprises:
    compressing a gas into a pressurized gas;
    drying the pressurized gas to obtain a dried pressurized gas; and
    decompressing the dried pressurized gas to obtain a gas of atmospheric pressure as the dry gas.

8. The method according to claim 7, wherein drying the pressurized gas comprises:
    removing a liquid from the pressurized gas; or
    removing a vapor from the pressurized gas.

9. The method of claim 1, wherein the spreading of the blood drop is done with a spreader.

10. The method of claim 1, wherein the slide has a long side extending between the one end and the another end.

11. The method of claim 1, wherein the flowing the dry gas is without turbulent flow.

12. The method of claim 1, wherein the dry gas is flowed in a pre-heated channel prior to flowing the dry gas over the major surface of the slide.

\* \* \* \* \*